United States Patent [19]

Dvornik et al.

[11] 4,423,075

[45] * Dec. 27, 1983

[54] ALDOSE REDUCTASE INHIBITION BY 5-FLUORO-2-METHYL-1-[[4-(METHYLSULFONYL)PHENYL]METHYLENE]-1H-INDENE-3-ACETIC ACID

[75] Inventors: Dushan M. Dvornik, Town of Mount Royal; Nicole Simard-Duquesne, Montreal, both of Canada

[73] Assignee: Ayerst, McKenna & Harrison Inc., Montreal, Canada

[ * ] Notice: The portion of the term of this patent subsequent to Dec. 22, 1998, has been disclaimed.

[21] Appl. No.: 332,567

[22] Filed: Dec. 21, 1981

Related U.S. Application Data

[63] Continuation-in-part of Ser. No. 160,873, Jun. 19, 1980, Pat. No. 4,307,114.

[51] Int. Cl.³ .............................................. A61K 31/19
[52] U.S. Cl. .................................................. 424/317
[58] Field of Search ......................................... 424/317

[56] References Cited

U.S. PATENT DOCUMENTS

| | | | |
|---|---|---|---|
| 3,647,858 | 3/1972 | Hinkley et al. | 260/470 |
| 3,654,349 | 4/1972 | Shen et al. | 260/515 M |
| 3,821,383 | 6/1974 | Sestanj et al. | 424/258 |

FOREIGN PATENT DOCUMENTS 3026402  2/1982  Fed. Rep. of Germany ...... 424/317

OTHER PUBLICATIONS

"Physicians Desk Reference", 34th ed. Medical Economics Co., Ordell, N.J., pp. 1147–1149.

J. R. Ryan et al., Clin. Pharmacol. Ther., 21, 231 (1977).

Primary Examiner—Frederick E. Waddell
Attorney, Agent, or Firm—Adley F. Mandel

[57] ABSTRACT

Disclosed are new methods of using 5-fluoro-2-methyl-1-[[4-(methylsulfonyl)phenyl]methylene]-1H-indene-3-acetic acid or a therapeutically acceptable salt thereof with an organic or inorganic base for the treatment of complications associated with diabetes mellitus. The compound inhibits lens aldose reductase in a diabetic mammal.

4 Claims, No Drawings

ALDOSE REDUCTASE INHIBITION BY 5-FLUORO-2-METHYL-1-[[4-(METHYLSULFONYL)PHENYL]METHYLENE]-1H-INDENE-3-ACETIC ACID

This application is a continuation-in-part of application Ser. No. 160,873, filed June 19, 1980, now U.S. Pat. No. 4,307,114, issued Dec. 22, 1981 and expressly incorporated herein by reference.

BACKGROUND OF THE INVENTION

This invention relates to new methods of using 5-fluoro-2-methyl-1-[[4-(methylsulfonyl)phenyl]methylene]-1H-indene-3-acetic acid or a therapeutically acceptable salt thereof with an organic or inorganic base for the treatment of complications associated with diabetes mellitus.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy and cataracts. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita et al., Biochem. Biophys. Acta, 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

5-Fluoro-2-methyl-1-[[4-(methylsulfonyl)phenyl]methylene]-1H-indene-3-acetic acid and its preparation are described by T.-Y. Shen et al., U.S. Pat. No. 3,654,349, issued Apr. 4, 1972 and D. F. Hinkley and J. B. Conn, U.S. Pat. No. 3,647,858, issued Mar. 7, 1972. 5-Fluoro-2-methyl-1-[[4-(methylsulfonyl)phenyl]methylene]-1H-indene-3-acetic acid has anti-inflamatory, anti-pyretic and analgesic activity, U.S. Pat. Nos. 3,654,349 and 3,647,858, cited above.

Surprisingly, 5-fluoro-2-methyl-1-[[4-(methylsulfonyl)phenyl]-methylene]-1H-indene-3-acetic acid or its therapeutically acceptable salt thereof with an organic or inorganic base, now has been found to be a potent inhibitor of lens aldose reductase. This new found property renders 5-fluoro-2-methyl-1-[[4-(methylsulfonyl)phenyl]methylene]-1H-indene-3-acetic acid, or a salt thereof, useful for the treatment of diabetic complications.

SUMMARY OF THE INVENTION

According to the present invention, a method is provided for preventing or relieving a diabetes mellitus associated condition in a diabetic mammal by administering to the mammal an alleviating or prophylatic amount of 5-fluoro-2-methyl-1-[[4-(methylsulfonyl)phenyl]methylene]-1H-indene-3-acetic acid or a therapeutically acceptable salt thereof with an organic or inorganic base. The latter compound is especially useful for preventing or relieving a diabetes mellitus associated complication consisting of cataracts, neuropathy, nephropathy and retinopathy in a diabetic mammal.

DETAILED DESCRIPTION OF THE INVENTION

5-Fluoro-2-methyl-1-[[4-(methylsulfonyl)phenyl]methylene]-1H-indene-3-acetic acid forms salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compound. Suitable inorganic bases to form these salts include, for example, the hydroxides, carbonates, bicarbonates or alkoxides of the therapeutically acceptable alkali metals or alkaline earth metals, for example, sodium, potassium, magnesium, calcium and the like. Suitable organic bases include the following amines; benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxylakyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve 5-fluoro-2-methyl-1-[[4-(methylsulfonyl)phenyl]methylene]-1H-indene-3-acetic acid in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, 5-fluoro-2-methyl-1-[[4-(methylsulfonyl)-phenyl]methylene]-1H-indene-3-acetic acid is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing 5-fluoro-2-methyl-1-[[4-(methylsulfonyl)phenyl]methylene]-1H-indene-3-acetic acid with an equivalent amount of the corresponding quaternary ammonium hydroxide in water solution, followed by evaporation of the water.

5-Fluoro-2-methyl-1-[[4-(methylsulfonyl)phenyl]methylene]-1H-indene-3-acetic acid or an addition salt thereof with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously 5-fluoro-2-methyl-1-[[4-(methylsulfonyl)phenyl]methylene]-1H-indene-3-acetic acid can be given orally. However, the method of administering 5-fluoro-2-methyl-1-[[4-(methylsulfonyl)phenyl]methylene]-1H-indene-3-acetic acid is not to be construed as limited to a particular mode of administration. For example, 5-fluoro-2-methyl-1-[[4-(methylsulfonyl)phenyl]methylene]-1H-indene-3-acetic acid can be administered topically directly to the eye in the form of drops of sterile, buffered opthalmic solutions, preferably of pH 7.2–7.6. Topical administration is especially useful for treating cataracts and retinopathy in a diabetic mammal. Also, it can be administered orally alone or in solid form containing such excipients as starch, milk sugar, certain types of clay and so forth. It can also be administered orally in the form of a solution or syrup, or it can be injected parenterally. For parenteral administration it can be used in the form of a sterile solution, preferably of pH 7.2–7.6 containing a pharmaceutically acceptable buffer. Oral and parenteral administration are the preferred routes for treating neuropathy and nephropathy in a diabetic mammal.

The dosage of the present therapeutic agent can vary with the form of administration. Furthermore, it can vary with the particular host under treatment. Generally, treatment is initiated with small dosages substantially less than the optimal dose of the compound. Thereafter, the dosage is increased by small increments until the optimal effect under the circumstances is reached. In general, 5-fluoro-2-methyl-1-[[4-(methylsulfonyl)phenyl]methylene]-1H-indene-3-acetic acid is most desirably administered at a concentration level that will generally afford effective results without causing any harmful or deleterious side effects. For topical administration, a 0.05 to 0.2% solution can be administered dropwise to the eye. The frequency of installation varies with the subject under treatment from a drop every two or three days to once daily. For oral or parenteral administration a preferred level of dosage ranges from about 0.1 mg to about 200 mg per kilogram of body weight per day, although aforementioned variations will occur. However, a dosage level that is in the range of from about 3.0 mg to about 30 mg per kilogram of body weight per day is most satisfactory.

Unit dosage forms such as capsules, tablets, pills and the like can contain from about 5 mg to about 50 mg of 5-fluoro-2-methyl-1-[[4-(methylsulfonyl)phenyl]methylene]-1H-indene-3-acetic acid dependent on the type of unit dosage, preferably with a significant quantity of a pharmaceutical carrier. Thus, for oral administration, capsules can contain from between about 5 mg to about 50 mg of 5-fluoro-2-methyl-1-[[4-(methylsulfonyl)phenyl]methylene]-1H-indene-3-acetic acid with or without a pharmaceutical diluent. Tablets, either effervescent or noneffervescent, can contain between about 5 to 50 mg of 5-fluoro-2-methyl-1-[[4-(methylsulfonyl)phenyl]methylene]-1H-indene-3-acetic acid together with conventional pharmaceutical carriers. Thus, tablets which can be coated and either effervescent or noneffervescent can be prepared according to the known art. Inert diluents or carriers, for example, magnesium carbonate or lactose, can be used together with conventional disintegrating agents, for example, maize starch and alginic acid and lubricating agents for example, magnesium stearate.

Syrups or elixirs suitable for oral administration can be prepared from water soluble salts, for example, the sodium salt of 5-fluoro-2-methyl-[[4-(methylsulfonyl)phenyl]methylene]-1H-indene-3-acetic acid and can advantageously contain glycerol and ethyl alcohol as solvents or preservatives.

The compositions and methods of administering 5-fluoro-2-methyl-1-[[4-(methylsulfonyl)phenyl]methylene]-1H-indene-3-acetic acid described in the above cited U.S. Pat. Nos. 3,654,349 and 3,647,858 can also be used in the treatment of complications associated with diabetes mellitus.

5-Fluoro-2-methyl-1-[[4-(methylsulfonyl)phenyl]methylene]-1H-indene-3-acetic acid, or a therapeutically acceptable salt thereof, also can be used in combination with insulin or oral hypoglycemic agents to produce beneficial effect in the treatment of diabetes mellitus. In this instance, commercially available insulin preparations or oral hypolycemic agents, exemplified by acetohexamide, chlorpropamide, tolazamide, tolbutamide and phenformin, are suitable. 5-Fluoro-2-methyl-1-[[4-(methylsulfonyl)phenyl]methylene]1H-indene-3-acetic acid, or a therapeutically acceptable salt thereof, can be administered sequentially or simultaneously with insulin or the oral hypoglycemic agent. Suitable methods of administration, composition and doses of the insulin preparation or oral hypoglycemic agent are described in medical textbooks; for instance, "Physicians' Desk Reference", 34 ed., Medical Economics Co., Oradell, N.J., U.S.A., 1980, "AMA Drug Evaluations", 3rd ed., PSG Publishing Co., Inc., Littleton, Mass., U.S.A., 1977, pp. 582–598, and "The Pharmacological Basis of Therapeutics", L. S. Goodman and A. Gilman, Eds., 5th ed., Macmillan Publishing Co., Inc., New York, N.Y., U.S.A., 1975, pp. 1507–1533. When used in combination, 5-fluoro-2-methyl-1-[[4-(methylsulfonyl)phenyl]methylene]-1H-indene-3-acetic acid, or its therapeutically acceptable salt, is administered as described previously. 5-Fluoro-2-methyl-1-[[4-(methylsulfonyl)-phenyl]methylene]-1H-indene-3-acetic acid, or its therapeutically acceptable salt, can be administered with the oral hypoglycemic agent in the form of a pharmaceutical composition comprising effective amounts of each agent.

The aldose reductase inhibiting effects of 5-fluoro-2-methyl-1-[[4-(methylsulfonyl)phenyl]methylene]-1H-indene-3-acetic acid or its pharmaceutically acceptable salts with an organic or inorganic base can be demonstrated by employing an in vitro testing procedure similar to that described by S. Hayman and J. H. Kinoshita, J. Biol Chem., 240, 877 (1965). In the present case the procedure of Hayman and Kinoshita is modified in that the final chromatography step is omitted in the preparation of the enzyme from bovine lens.

When evaluated in the above in vitro test, 5-fluoro-2-methyl-1-[[4-(methylsulfonyl)phenyl]methylene]-1H-indene-3-acetic acid exhibited a 50 percent inhibition at a concentration of $5 \times 10^{-7}$ M.

The aldose reductase inhibiting property of 5-fluoro-2-methyl-1-[[4-(methylsulfonyl)phenyl]methylene]-1H-indene-3-acetic acid and its utilization in diminishing and alleviating diabetic complications also are demonstrable in experiments using galactosaemic rats, see D. Dvornik et al., Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent laboratory chow, Purina) and glucose at 20% (w/w %) concentration. The untreated galactosaemic group was fed a similar diet in which galactose is substituted for glucose. The other groups were fed diets containing various amounts of 5-fluoro-2-methyl-1-[[4-(methylsulfonyl)phenyl]methylene]-1H-indene-3-acetic acid in the galactose containing diet. The concentration of galactose in the diet of the treated groups was the same as that for the untreated galactosaemic group.

(b) After four days, the animals were killed by decapitation. The eyeballs were removed and punctured with a razor blade; the freed lenses were rolled gently on filter paper and weighted. The sciatic nerves were dissected as completely as possible and weighed. Both tissues were frozen and kept up to two weeks before being analyzed for dulcitol.

(c) The tissues were homoginized in 5% (w/v) trichloroacetic acid and the polyol determination on the extracts was performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was substracted from the individual values found in the corresponding rat tissue to obtain the amount of polyol accumulated].

The following results show that 5-fluoro-2-methyl-1-[[4-(methylsulfonyl)phenyl]methylene]-1H-indene-3-acetic acid diminishes and alleviates the accumulation of galactitol in the lenses and sciatic nerves of rats fed galactose as compared to an untreated animal: at a dose of 91 mg/kg/day exhibited a 27±9 percent decrease in galactitol accumulation in the lens and a 45±9 percent decrease in galactitol accumulation in the sciatic nerve.

We claim:

1. A method of preventing or relieving a diabetic complication in a diabetic mammal which comprises administering to said mammal an effective alleviating or prophylactic amount of 5-fluoro-2-methyl-1-[[4-(methylsulfonyl)phenyl]methylene]-1H-indene-3-acetic acid, or a therapeutically acceptable salt thereof with an organic or inorganic base.

2. The method of claim 1 wherein said diabetic complication is selected from cataracts, neuropathy, nephropathy and retinopathy.

3. A method of preventing or relieving diabetes mellitus associated complications consisting of cataracts and retinopathy in a diabetic mammal which comprises topically administering to said mammal an effective alleviating or prophylactic amount of a sterile aqueous solution of 5-fluoro-2-methyl-1-[[4-(methylsulfonyl)phenyl]methylene]-1H-indene-3-acetic acid, or a therapeutically acceptable salt thereof with an organic or inorganic base.

4. A method of preventing or relieving diabetes mellitus associated complications consisting of neuropathy and nephropathy in a diabetic mammal which comprises orally or parenterally administering to said mammal an effective alleviating or prophylactic amount of 5-fluoro-2-methyl-1-[[4-(methylsulfonyl)phenyl]methylene]-1H-indene-3-acetic acid, or a therapeutically acceptable salt thereof with an organic or inorganic base.

* * * * *